United States Patent [19]

Rudie

[11] Patent Number: 5,776,176
[45] Date of Patent: Jul. 7, 1998

[54] MICROWAVE ANTENNA FOR ARTERIAL FOR ARTERIAL MICROWAVE APPLICATOR

[75] Inventor: Eric N. Rudie, Maple Grove, Minn.

[73] Assignee: Urologix Inc., Minneapolis, Minn.

[21] Appl. No.: 672,505

[22] Filed: Jun. 17, 1996

[51] Int. Cl.⁶ .................................................. A61N 5/02
[52] U.S. Cl. .................... 607/101; 607/105; 607/100; 607/104; 607/116; 607/154
[58] Field of Search .............................. 607/101, 102, 607/105, 113, 156, 99, 100, 104, 116, 154; 128/639, 642

[56] References Cited

U.S. PATENT DOCUMENTS

| | | | |
|---|---|---|---|
| 4,557,272 | 12/1985 | Carr | 128/736 |
| 4,559,951 | 12/1985 | Dahl et al. | 128/642 |
| 4,825,880 | 5/1989 | Stauffer et al. | 128/804 |
| 4,832,047 | 5/1989 | Sepetka et al. | 128/772 |
| 4,841,988 | 6/1989 | Fetter et al. | 128/804 |
| 4,945,318 | 7/1990 | Kabachinski et al. | 333/12 |
| 5,026,959 | 6/1991 | Ito et al. | 219/10.55 |
| 5,057,106 | 10/1991 | Kasevich et al. | 606/33 |
| 5,246,438 | 9/1993 | Langberg | 606/33 |
| 5,281,217 | 1/1994 | Edwards et al. | 606/41 |
| 5,300,099 | 4/1994 | Rudie | 607/101 |
| 5,344,435 | 9/1994 | Turner et al. | 607/101 |
| 5,364,392 | 11/1994 | Warner et al. | 606/34 |
| 5,370,676 | 12/1994 | Sozanski et al. | 607/101 |
| 5,370,678 | 12/1994 | Edwards et al. | 607/101 |
| 5,405,346 | 4/1995 | Grundy et al. | 606/41 |
| 5,413,588 | 5/1995 | Rudie et al. | 607/101 |
| 5,423,811 | 6/1995 | Imran et al. | 606/41 |
| 5,462,521 | 10/1995 | Brucker et al. | 604/20 |
| 5,620,480 | 4/1997 | Rudie | 607/101 |
| 5,628,770 | 5/1997 | Thome et al. | 607/101 |
| 5,643,335 | 7/1997 | Reid et al. | 607/101 |
| 5,649,973 | 7/1997 | Tierney et al. | 607/101 |

FOREIGN PATENT DOCUMENTS

| | | |
|---|---|---|
| 0 462 302 A1 | 6/1990 | European Pat. Off. |
| WO 94/26188 | 11/1994 | WIPO |
| WO 95/05869 | 3/1995 | WIPO |

OTHER PUBLICATIONS

"Introduction to Hyperthermia Device Evaluation" by M.D. Sapozink et al, *International Journal of Hyperthermia*, 1988, vol. 4, No. 1, 1–15.

"Implantable Helical Coil Microwave Antenna for Interstitial Hyperthermia" by Torusatoh et al, *International Journal of Hyperthermia*, 1988, vol. 4, No. 5.497–512.

"Heating Characteristics of a Helical Microwave Applicator for Transurethral Hyperthermia of Benign Prostatic Hyperplasia" by M. Astrahan et al, *International Journal of Hyperthermia*, 1991, vol. 7, No. 1, 141–155.

"A Dipole Antenna for Interstitial Microwave Hyperthermia" by W. Hurter et al, *IEEE Transactions on Microwave Theory and Techniques*, vol. 39, No. 6, Jun. 1991.

*Primary Examiner*—Robert L. Nasser
*Assistant Examiner*—Stephen Huang
*Attorney, Agent, or Firm*—Kinney & Lange, P.A.

[57] ABSTRACT

A microwave antenna is insertable into a cardiovascular catheter and is formed from a coaxial cable including an inner conductor and an inner insulator with the inner insulator having a reduced diameter portion adjacent a distal end of the catheter. An antenna coil portion of the microwave antenna is disposed about the reduced diameter portion and has a first section, a second section, and a point intermediate to the first and second sections. The intermediate point is electrically connected to an outer conductor of the coaxial cable. An impedance matching means is connected to the inner conductor and to the second section of the antenna coil portion.

22 Claims, 7 Drawing Sheets

MICROWAVE ANTENNA FOR ARTERIAL FOR ARTERIAL MICROWAVE APPLICATOR

REFERENCE TO CO-PENDING APPLICATIONS

Reference is hereby made to copending application Ser. No. 08/621,634, filed Mar. 26, 1996, and application Serial No. 08/672504, filed concurrently herewith and titled ARTERIAL MICROWAVE APPLICATOR.

BACKGROUND OF THE INVENTION

The present invention relates to the field of microwave thermal ablation therapy of tissue. In particular, the present invention relates to a microwave antenna for placement in a cardiovascular catheter for microwave thermal ablation therapy of cardiac tissue.

Cardiac arrhythmias are one type of irregular beating of the heart which can result from damage caused to a portion of cardiac tissue. Specifically, cardiac arrhythmias result when damaged cardiac tissue (e.g., along a ventricle or atrial wall) prevents the proper conduction of an electrical and rhythmic impulse through the ventricle wall or atrial wall in the region of damaged tissue. This disruption of the electrical and rhythmical impulse inhibits the chambers of the heart from contracting and expanding with the proper timing and the proper force.

Cardiac arrhythmias have traditionally been treated with medication and/or through surgery. However, medications are limited in their application since they are successful in treating only certain types of cardiac arrhythmlas. On the other hand, while a portion of cardiac tissue which is damaged can be surgically removed, surgery carries much more risk than medicinal treatment of cardiac arrhythmias.

Alternative methods of treating cardiac arrhythmias include applying heat to the damaged cardiac tissue by inserting a catheter into a chamber of the heart, e.g., ventricle, and using the catheter to apply heat locally to ablate the damaged portion of cardiac tissue to neutralize its effect on the electrical and rhythmical impulse. For example, Fram PCT International Publication WO 94/07446, published Apr. 14, 1994, discloses a catheter and method for ablating electrically conductive pathways of a heart. This catheter includes a balloon mounted on a catheter shaft and a heating device located within the balloon to heat the fluid inside the balloon. The heated fluid heats the cardiac tissue by thermal conduction from the balloon fluid to the tissue through a wall of the balloon. This technique carries several disadvantages. First, since this method uses thermal conduction, the surface of the cardiac tissue immediately adjacent the outer surface of the balloon is necessarily heated yet cardiac tissue deep below the surface, where lesions are frequently located, remains unheated. Second, since the catheter necessarily heats the surface of the cardiac tissue, any healthy tissue on the surface of a wall of the cardiac chamber is unnecessarily damaged. Finally, this method of applying heat to cardiac tissue unnecessarily heats blood in the cardiac chamber (e.g., ventricle) surrounding a side of the catheter opposite a wall of the chamber. This technique can coagulate small portions of blood that pass through the particular chamber of the heart adjacent the catheter, thereby producing clotting and emboli in the bloodstream.

Other catheters ablate cardiac tissue using radio frequency or microwave energy that is transmitted from a distal end of the catheter through cardiac tissue to the site to be treated. Langberg 4,945,912 discloses a catheter including a microwave antenna for directing microwave energy to ablate cardiac tissue. The goal of these catheters is to transmit energy deeper into the cardiac tissue than is possible with conventional thermal conduction methods such as those disclosed in the Fram PCT Publication. However, these catheters also unnecessarily necrose healthy tissue immediately adjacent an outer surface of the catheter.

In an attempt to limit heating of tissue immediately adjacent a heat generating portion of a catheter, some cardiac ablation catheters include cooling systems incorporated into the catheter adjacent the heat generating portion of the catheter. Nardella, U.S. Pat. No. 5,334,193, discloses an ablation catheter which includes at its distal end, an electrode for directing radio frequency energy (RF) to necrose damaged cardiac tissue and a cooling lumen centrally aligned throughout the catheter for delivering cooling fluid adjacent the electrode for limiting heat transferred by the electrodes to adjacent tissues.

Other methods of protecting healthy tissue from the heat generated by an electrode of a microwave ablation catheter include attempts to selectively block the propagation of the microwave field generated by the electrode. Stern et al., U.S. Pat. No. 5,314,466, discloses a microwave ablation catheter including a structure for blocking the propagation of a microwave field in a desired direction to prevent undesired heating of blood within the cardiac chamber which surrounds the heat producing end of the catheter. This catheter also has a mechanism for pivoting a distal portion of its catheter relative to a remaining proximal portion of the catheter to orient the microwave field in a desired orientation relative to the tissue site to be treated.

Previous cardiac ablation catheters have attempted to limit the heat applied to tissues and/or blood immediately surrounding the heat producing end of the catheter. However, thus far, previous catheters have, failed to: (1) deliver adequate microwave energy in cardiac tissue at depths which actually necrose the damaged tissue; (2) adequately cool healthy tissue immediately adjacent the microwave energy producing portion of the catheter; and (3) adequately protect a cardiac environment, such as blood, immediately surrounding an outer surface of the microwave energy producing portion of the catheter.

SUMMARY OF THE INVENTION

A microwave antenna is insertable into a cardiovascular catheter and is formed from a coaxial cable including an inner conductor and an inner insulator with the inner insulator having a reduced diameter portion adjacent a distal end of the catheter. An antenna coil portion of the microwave antenna is disposed about the reduced diameter portion and has a first section, a second section, and a point intermediate to the first and second sections. The intermediate point is electrically connected to an outer conductor of the coaxial cable. An impedance matching means is connected to the inner conductor and to the second section of the antenna coil portion.

This antenna structure enables the catheter of the present invention to deliver microwave energy at depths well below the cardiac chamber wall surface due to: (1) its good impedance matching (which miminiizes reflective losses); (2) good current carrying capability; and (3) due to the antenna having an effective electrical length which is generally one-half of the wavelength of the radiation emitted in the surrounding medium and which is independent of the physical length of the antenna. This latter feature allows the antenna and catheter to be made with different physical lengths while still maintaining the same effective electrical length for predictability in microwave energy radiation application. The reduced diameter portion of the inner insulator permits the antenna to have a low profile to facilitate advancement of the catheter through the cardiovascular system for distally remote cardiac applications.

BRIEF DESCRIPTION OF THE DRAWINGS

FIG. 9 a sectional view of a ventricle of a human heart showing a portion of damaged cardiac tissue.

DETAILED DESCRIPTION OF THE PREFERRED EMBODIMENTS

Figure 1:
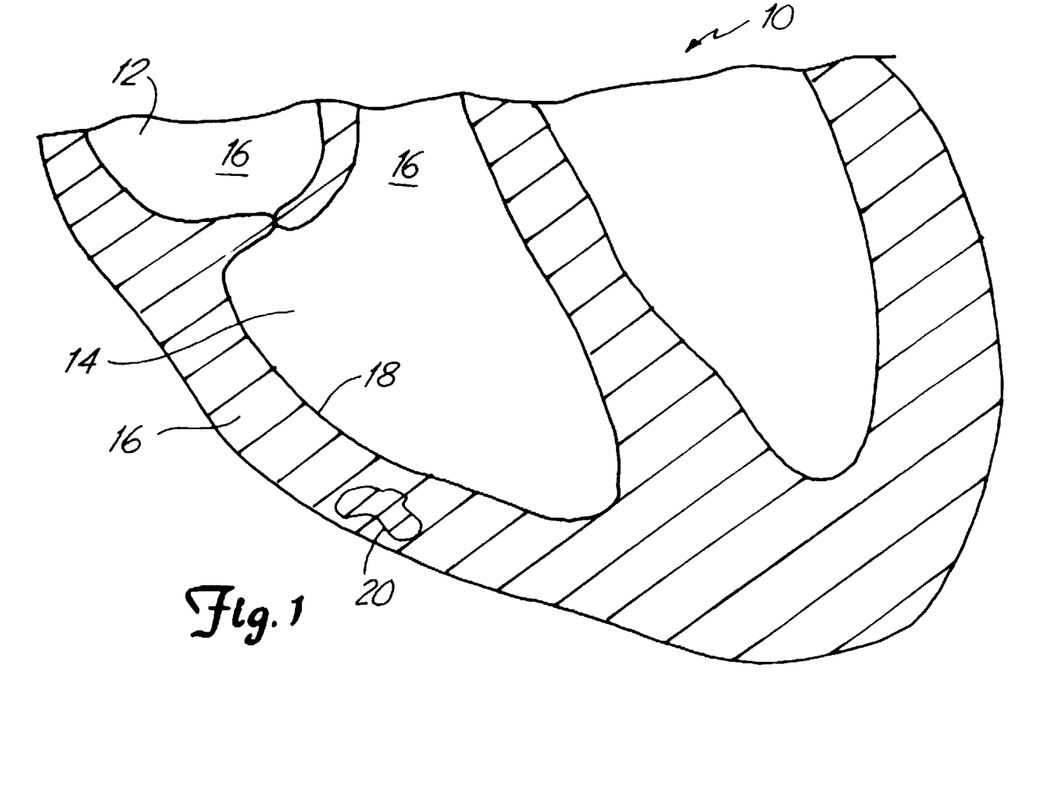

FIG. 1 is a vertical sectional view of a human heart showing a location of damaged tissue which can cause cardiac arrhythmia. Heart 10 includes right atrium 12, right ventricle 14, and blood 15 within atrium 12 and ventricle 14. Ventricle 14 includes wall 16, surface 18, and damaged tissue 20. The damaged tissue 20 of ventricle wall 16 which causes cardiac arrhythmias, such as ventricular tachycardia, can be effectively removed by heating and necrosing damaged tissue 20. Ideally, with the present invention, only damaged tissue 20 of ventricle wall 16 spaced from surface 18 is heated and necrosed while, at the same time, damage to ventricle wall surface 18 and to blood 15 is prevented. A selective thermal heating of damaged tissue 20 of ventricle wall 16 is made possible by microwave antenna-containing catheter 28 of the present invention, which is shown in FIG. 2.

Figure 2:
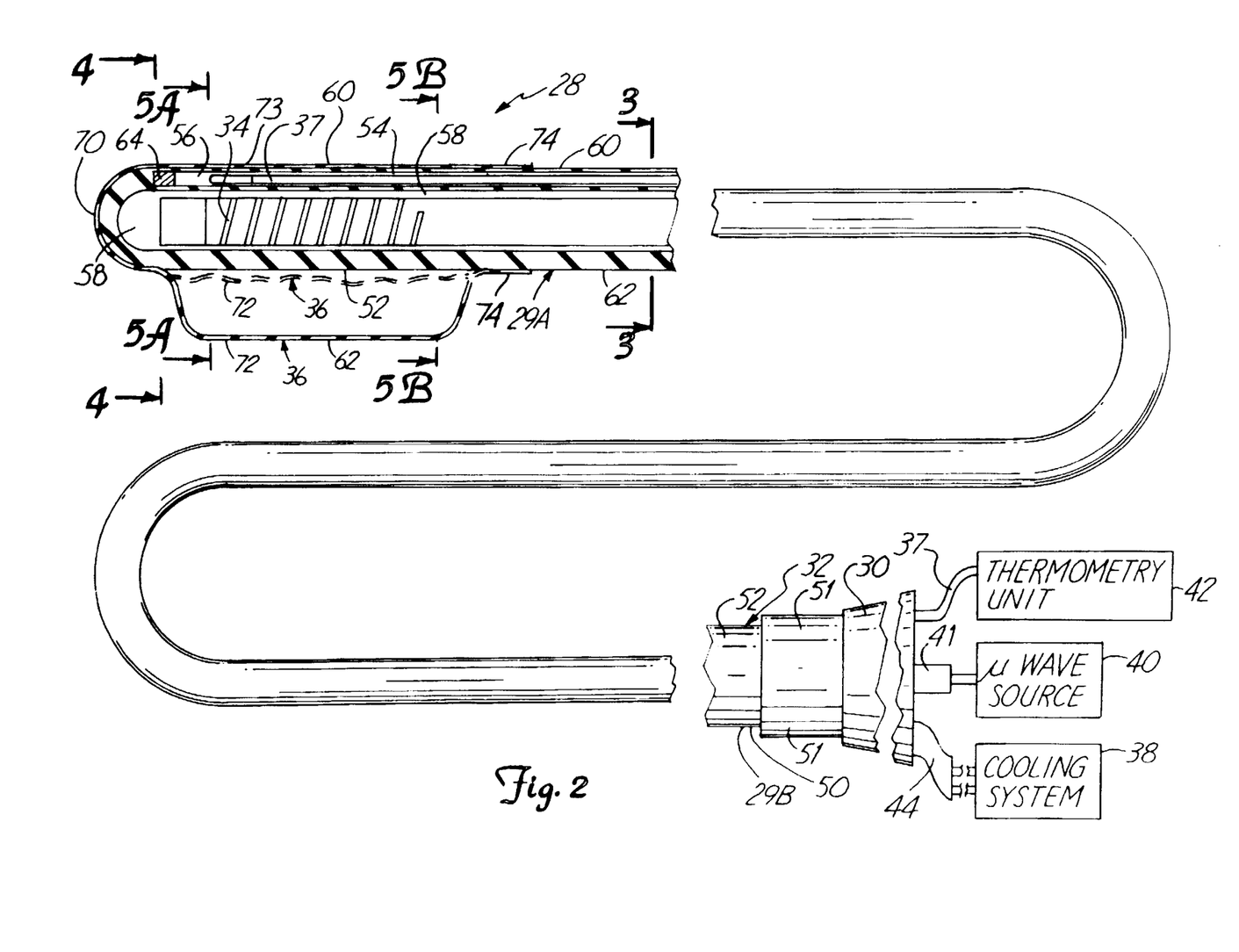
FIG. 2 is a Sectional view of an intravascular ablation catheter of the present invention with a proximal end and a distal end of the catheter enlarged for clarity.

FIG. 2 shows a side view of catheter 28 including a sectional view of a distal end 29A of catheter 28 and a plan view of a proximal end 29B of catheter 28. Both distal end 29A and proximal end 29B are enlarged relative to shaft 32 of catheter 28 for illustrative purposes. As shown in FIG. 2, catheter 28 generally includes manifold 30, multi-lumen shaft 32, microwave antenna 34, cooling balloon 36, and thermometry sensor 37. Catheter 28 is used with cooling system 38, microwave generating source 40, and thermometry unit 42.

Manifold 30 receives coaxial cable 41 (from microwave generating source 40), thermometry sensor 37, and cooling system delivery tubing 44 for alignment with corresponding lumens within shaft 32. Shaft 32 is an extruded multi-lumen, intravascular catheter shaft connected to manifold 30 at proximal shaft end 50 via strain relief member 51.

Manifold 30 and shaft 32 are preferably made of a polymeric material such as polyethylene terephthalate (PET) sold by ATOCHEM, INC. (Glen Rock, N.J.) under the trademark PEBAXO or sold by Consolidated Polymers, Inc. under the tradename C-FLEX. The polymeric material preferably has a hardness of about 20 to about 80 on the Shore D hardness scale.

Shaft 32 also includes outer surface 52. In one preferred embodiment, shaft 32 includes a coating (e.g., TEFLON®) having a low coefficient of friction well known in the art forming outer surface 52 of shaft 32 to facilitate its advancement through a guide catheter positioned within the vascular system. Shaft 32 has an outer diameter of about 0.1 inches, suitable for insertion within a 10 French size guide catheter. Shaft 32 is long enough (e.g., 135 centimeters) and of a small enough diameter to permit insertion of distal shaft end 54 through the vascular system and into ventricle 14 (FIG. 1). Manifold 30 preferably has a length of about 2 inches.

A proximal portion of shaft 32 can be augmented with additional design features well known to those skilled in the art to provide adequate steerability, size, pushability, tracking, and biocompatibility. In addition, the catheter polymer material forming shaft 32 can include a radiopaque filler material well known in the art (e.g., bismuth subcarbonate or barium sulfate) to facilitate visualization of catheter shaft 32 under fluoroscopy.

As shown in FIG. 2, shaft 32 also includes temperature sensing lumen 56, and microwave antenna lumen 58. Lumens 56 and 58 generally extend from proximal shaft end 50 to distal shaft end 54.

Temperature sensing lumen 56 is positioned near first side 60 of shaft 32. Temperature sensing lumen 56 permits insertion of thermnometry sensor 37 within shaft 32 to monitor the temperature of adjacent tissue when shaft 32 is inserted within ventricle 14. Sensor 37- exits through manifold 30 and is connected to thermometry unit 42. In a preferred embodiment, thermometry sensor 37 is a fiber optic luminescence type temperature sensor sold by Luxtron Corporation.

Microwave antenna lumen 58 is aligned centrally relative to the longitudinal axis of shaft 32 along a majority of the length of shaft 32, antenna lumen 58 being equidistant between first side 60 of shaft 32 and second side 62 of shaft 32. However, at the distal-most end of shaft 32, adjacent cooling balloon 36, antenna lumen 58 effectively becomes oriented nearer first side 60 than second side 62 due to the presence of cooling balloon 36.. At its proximal end, antenna lumen 58 communicates with manifold 30.

Antenna lumen 58 is adapted for receiving microwave antenna 34 to be permanently positioned within antenna lumen 58 near cooling balloon 36 so that antenna 34 will be generally situated adjacent damaged tissue 20 of ventricle wall 16 when shaft 32 is properly positioned within heart 10. Antenna 34 can be bonded within antenna lumen 58 by an adhesive bond and is carried at the distal-most end of coaxial cable 41. The proximal-most end of coaxial cable 41 is connected to microwave generating source 40. Microwave generating source 40 produces high frequency microwaves, preferably at about 915 MHz. When antenna 34 is energized by microwave generating source 40, antenna 34 emits electromagnetic energy which causes heating of tissue within ventricle wall 16 at target location 20 (FIG. 1).

Cooling balloon 36 cooperates with multi-lumen shaft and is secured about distal end 54 of catheter shaft 32. Cooling balloon 36 is provided so that when filled with a cooling fluid, cooling balloon 36 absorbs microwave energy emitted by antenna 34 to prevent unwanted heating of blood on second side 62 of catheter 28 within a cardiac chamber of the heart while microwave energy radiating from a first side of catheter 28 heats damaged tissue 20. Cooling balloon 36 cools blood immediately surrounding and passing by the cooling balloon 36.

Cooling balloon 36 includes distal tip end 70, expandable wall portion 72, connection portion 73 and proximal waist end 74. Balloon 36 is secured over shaft 32 by slip-fitting balloon 36 over the distal end 54 of the catheter shaft 32. Distal tip end 70 of balloon 36 is then adhesively bonded to exterior surface 52 of shaft 32 at distal shaft end 54. Connection portion 73 of cooling balloon 36 is adhesively bonded to outer surface 52 on shaft first side 60 while proximal waist 74 of cooling balloon 36 is adhesive bonded to outer surface 52 on both shaft sides 60 and 62.

This arrangement creates a sealed connection at distal end 70, proximal end 74, and along connection portion 73 to secure cooling balloon 36 on catheter shaft 32. An inner surface of expandable portion 72 is spaced from and is not secured to shaft outer surface 52 so that expandable portion 72 remains free to expand relative to catheter outer surface 52 upon introduction and passage of an inflation cooling fluid through an interior of cooling balloon 36. With cooling balloon 36 secured in this manner, outer surface 52 of catheter second side 62 and expandable portion 72 effectively define a cooling chamber which can be inflated (as seen in FIG. 2) and deflated (shown in phantom in FIG. 2) by the selective introduction and removal of an inflation fluid within an interior of expandable wall portion 72. Expandable portion 72 of cooling balloon 36 is positioned adjacent to microwave antenna 34 so that in use, cooling fluid within cooling balloon 36 will cool blood surrounding catheter second side 62 and absorb microwave energy radiating towards second side 62 when antenna 35 is energized.

Cooling balloon 36 extends for a length adjacent distal shaft end 54 that is substantially less than the length of catheter shaft 32, yet equal to or greater than a length of microwave antenna 34. Moreover, cooling balloon 36 has a length less than an entire length of the ventricle wall (shown in FIG. 1). For example, cooling balloon 36 preferably has a length of about 1 to 2.5 centimeters with expandable wall portion 72 preferably having a length of about 0.5 to 2 centimeters. Balloon 36 is a flexible tubular member formed of PET, cross-linked polyethylene or some other thermoplastic material that acts as a low-compliance balloon material.

Figure 3:
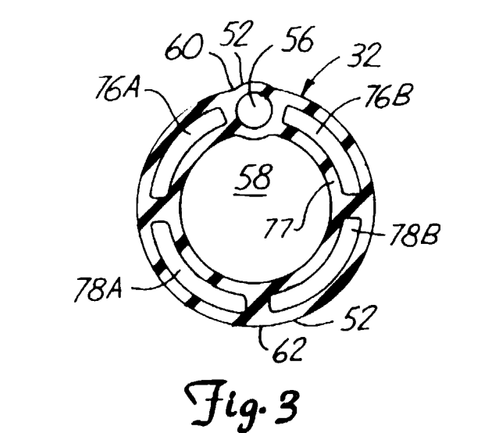
FIG. 3) is a sectional view of a shaft of the catheter of FIG. 2 taken along lines 3—3.

Cooling balloon 36 cooperates with multi-lumen shaft 32. As shown in FIG. 3, shaft 32 further includes cooling lumens 76A, 76B and cooling lumens 78A, 78B in addition to temperature sensing lumen 56 and antenna lumen 58. Temperature sensing lumen 56 preferably has a generally circular shaped transverse cross-section with a diameter of about 0.02 inches and an outer surface radius (defined by outer surface 52) of about 0.013 inches. Microwave antenna lumen 58 preferably has a generally circular shaped transverse cross-sectional area which is substantially larger than a transverse cross-sectional area of any other respective lumen of catheter shaft 32. Antenna lumen 58 preferably has a diameter of about 0.060 inches.

Cooling fluid intake lumens 76A, 76B are positioned adjacent shaft first side 60 between first side 60 and antenna lumen 58 while cooling fluid exhaust lumens 78A, 78B are positioned adjacent shaft second side 62 between second side 62 and antenna lumen 58. Cooling fluid intake lumens 76A, 76B and exhaust lumens 78A, 78B extend from proximal shaft end 50 to distal shaft end 54 where lumens 76A, 76B and 78A, 78B terminate. Cooling fluid intake lumens 76A, 76B and exhaust lumens 78A, 78B are defined by single wall 77 having a uniform thickness and preferably have a generally arc shaped transverse cross-section configured to surround antenna lumen 58. Cooling lumens 76A, 76B and 78A, 78B preferably have a uniform radial thickness of about 0.010 inches defined by an inner radius of about 0.035 inches and an outer radius of about 0.045 inches. In combination, cooling lumens 76A, 76B and cooling lumens 78A, 78B substantially surround antenna lumen 58 about a substantial majority (about 75%) of a circumference of antenna lumen 58. Cooling lumens 76A, 76B and 78A, 78B surround antenna lumen 58, so that when filled with a cooling fluid, cooling exhaust lumens 78A and 78B absorb microwave energy emitted by antenna 34 (within antenna lumen 58) to protect blood immediately surrounding catheter shaft second side 62 and cooling intake lumens 76A, 76B cool tissues immediately adjacent catheter shaft first side 60.

Figure 4:
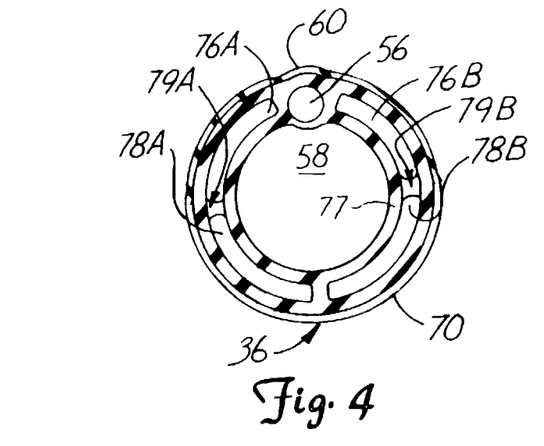
FIG. 4 is a sectional view of the catheter shaft of FIG. 2 taken along lines 4—4.

Cooling fluid intake lumens 76A and 76B communicate with cooling exhaust lumens 78A and 78B, respectively, near distal shaft end 54 of catheter shaft 32 distal to expandable portion 72 of cooling balloon 36 (FIG. 2). As shown in FIG. 4, catheter wall 77 includes holes 79A and 79B and distal portion 70 of cooling balloon 36 is secured to catheter shaft outer surface 52. Hole 79A in catheter wall 77 permits communication between cooling intake lumen 76A and cooling exhaust lumen 78A while hole 79B in catheter wall 77 permits communication between cooling intake lumen 76B and cooling exhaust lumen 78B. Cooling intakes lumens 76A and 76B and cooling exhaust lumens 78A and 78B cooperate with cooling system 38 (via manifold 30) to provide a selectively controlled flow of fluid through cooling lumens 76A, 76B, 78A, and 78B during a treatment session. For example, in one embodiment, intake lumens 76A, 76B and exhaust lumens 78A, 78B are supplied with deionized water from cooling system 38. Water from cooling system 38 is chilled to between about 12°–15° C. and pumped through cooling fluid intake lumens 76A, 76B toward distal shaft end 54. Under fluid pressure, water enters cooling fluid exhaust lumens 78A, 78B through holes 79A, 79B and returns to cooling system 38 through exhaust lumens 78A, 78B for re-chilling and re-circulation.

Figure 5A:
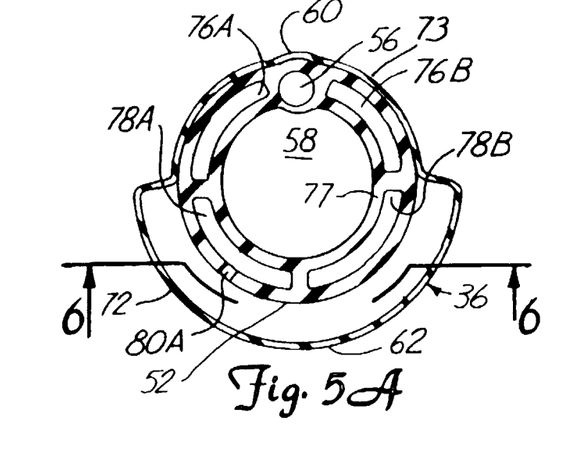
FIG. 5A is a sectional view of the catheter shaft of FIG. 2 taken along lines 5A—5A.
Figure 5B:
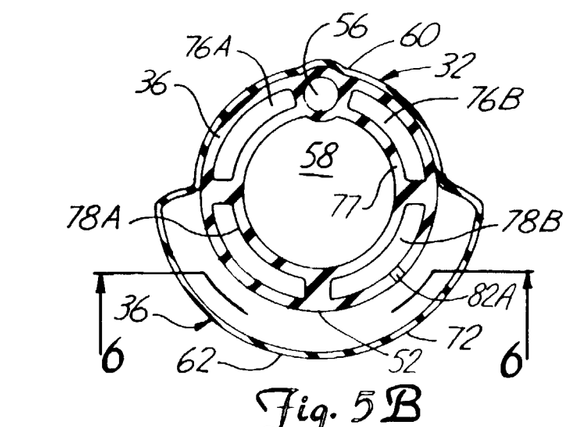
FIG. 5B is a sectional view of the catheter shaft of FIG. 2 taken along lines 5B—5B.

FIGS. 5A and 5B illustrate communication between cooling balloon 36 and cooling exhaust lumens 78A, 78B. FIGS. 5A and 5B are crosssectional views of shaft 32 taken along lines 5A—5A and 5B—5B in FIG. 2. As seen in FIG. 5A, cooling balloon 36 surrounds shaft outer surface 52 on shaft second side 62 with expandable portion 72 preferably having a generally arc shaped transverse cross-section (when inflated). Connection portion 73 of cooling balloon 36 is secured to shaft first side 60 while expandable portion 72 is spaced from and substantially surrounds entire second side 62 including cooling fluid exhaust lumens 78A, 78B. Cooling balloon 36 has a wall thickness of about 0.0005 to 0.005 inches, which is generally less than a wall thickness of wall 77 (e.g., 0.005 inches) defining cooling lumens 76A–78B. The cooling chamber defined between catheter outer surface 52 and expandable portion 72 of cooling balloon 36 has a radial thickness of about 0.5 to 5.0 millimeters, which is substantially greater than a radial thickness of cooling exhaust lumens 78A, 78B (e.g., 0.25 millimeters). Accordingly, expandable portion 72 of cooling balloon 36 (when inflated) defines a cooling chamber that has a transverse cross-sectional area substantially greater than the transverse cross-sectional area of cooling exhaust lumens 78A, 78B.

Figure 6:
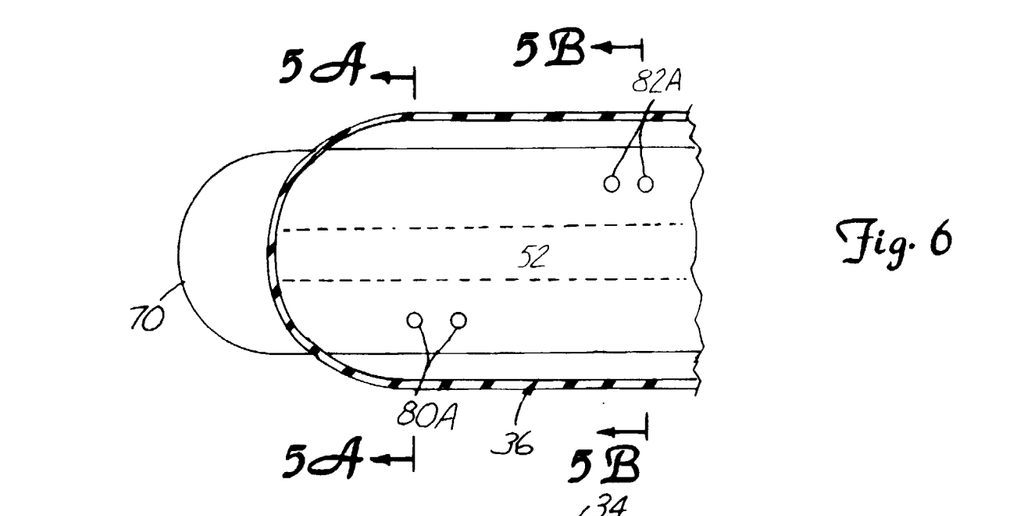
FIG. 6 is a plain view of a second side of the catheter shaft shown in FIGS. 5A and 5B with a balloon portion removed and as taken along lines 6—6.

As further shown in FIG. 5A, an outer wall of cooling exhaust lumen 78A includes hole 80A and as shown in FIG. 5B, an outer wall of cooling exhaust lumen 78B includes hole 82A. Hole 80A permits communication between exhaust lumen 78A and an interior of cooling balloon 36 while hole 82A permits communication between an interior of cooling balloon 36 and exhaust lumen 78B. Since fluid is flowing under pressure into cooling lumens 78A and 78B, fluid within lumen 78A enters inflatable cooling balloon 36 via hole 80A, passes through cooling balloon 36 and exits into exhaust lumen 78B via hole 82A to recirculate through cooling system 38 via manifold 30. As shown in FIG. 6, holes 80A and 80B are both axially and laterally spaced apart. This arrangement creates a pressure differential between the respective holes 80A and 80B causing a passive inflation of the cooling balloon 36 and insuring that adequate fluid circulation will occur through cooling balloon 36 as cooling fluid moves through cooling lumens 76A, 76B and 78A, 78B.

In addition, the rate of cooling fluid intake into lumens 76A, 76B and the rate of cooling fluid exhaust out of lumens 78A, 78B can be manipulated by cooling system 38 via manifold 30 to selectively modify the fluid pressure gradient between hole 80A and hole 80B to maintain cooling balloon 36 in an inflated state and to ensure a constant circulation of cooling fluid therethrough. The relative sizing of holes 80A and 80B, respectively, also can be modified to control the flow of cooling fluid in and out of the cooling balloon 36. For example, hole 80A can be made larger than hole 80B to accentuate filling of cooling balloon 36.

Figure 7:
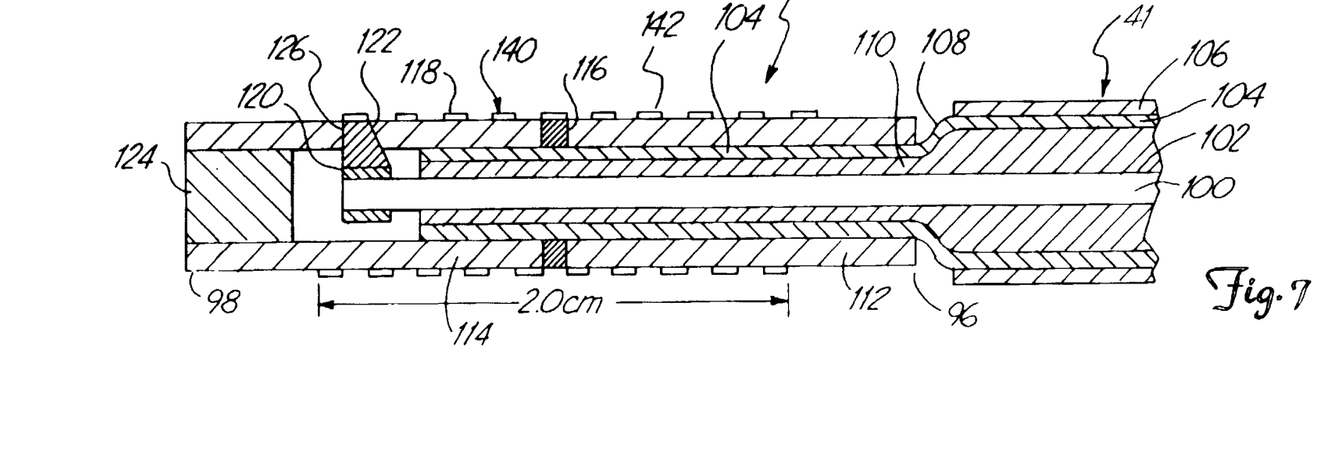
FIG. 7 is an enlarged sectional view of a microwave antenna incorporated into catheter of the present invention.

The microwave radiation used to ablate target tissue 20 (FIG. 1) is emitted by microwave antenna 34. FIG. 7 illustrates microwave antenna 34 in detail. Microwave antenna 34 is adapted for employment in cardiovascular applications, and therefore is designed to have a low profile (minimal outer diameter) while still providing efficient powerful emission of microwave energy to selectively ablate targeted cardiac tissue 20. In particular, antenna 34 is designed so that an outer diameter of antenna 34 is no greater than an outer diameter of coaxial cable 41, and so that antenna 34 is relatively short, e.g., about 2–3 centimeters. As previously described, microwave antenna 34 is positioned within microwave antenna lumen 58 and is surrounded by cooling lumens 76A, 76B, 78A, 78B and cooling balloon 36.

FIG. 7 illustrates a sectional view of microwave antenna 34. Antenna 34 is positioned at the distal most end of shielded coaxial cable 41. Cable 41 is a standard miniature 30 AWG or 32 AWG coaxial cable and can be obtained from CoonerWire of Chatsworth, Calif. Coaxial cable 41 includes inner conductor 100, inner insulator 102, outer conductor 104, and outer insulator 106. Antenna 34 further includes transition portion 108, reduced diameter portion 110 of inner insulator 102, first tubular extension 112, second tubular extension 114, and annular collar 116. Antenna 34 also includes a flat wire coil 118, capacitor 120, solder 122, and end cap 124.

First tubular extension 112 encompasses outer conductor 104 and reduced diameter portion 110 of inner insulator 102. A proximal end of tubular extension 112 is positioned adjacent transition portion 108 of cable 41. Annular collar 116 also encompasses outer conductor 104 and reduced diameter portion 110 of inner insulator 102 and abuts a distal end of tubular extension 112. Annular collar 116 is a conductive material that is in electrical contact with outer conductor 104. Second tubular extension 114 also encompasses outer conductor 104 and reduced diameter portion 110 of inner insulator 102 with a proximal end of second tubular extension 114 abutting annular collar 116. A distal end of second tubular extension 114 has end cap 124 disposed therein.

Flat wire 118 forms a coil about tubular extensions 112 and 114. Capacitor 120 is secured about a distal end of inner conductor 100 and is further electrically connected to flat wire coil 118 by solder 122 extending through hole 126.

Reduced diameter portion 110 preferably has a length of about 2 inches and an outer diameter of about 0.05 inches. Tubular extensions 112 and 114 have lengths of 1 inches and 0.8 inches, respectively, and can have a thickness of about 0.010 inches. Reduced diameter portion 110 and tubular extensions 112 and 114 have outer diameters (or thicknesses) of a size so that when antenna 34 is fully constructed, antenna 34 has an outer diameter of about 0.060 inches or less.

Antenna 34 includes a first coil section 140 and a second coil section 142, both of which are of equal length. These two sections are created by the electrical connection of annular collar 116 with flat wire coil 118 at a midsection of flat wire coil 118. In one embodiment, first and second coil sections 140 and 142 are each comprised of five equally-spaced windings of flat wire coil 118 about tubular extensions 112 and 114, respectively. The combined length of first and second coil sections 140 and 142 provide an overall length of antenna 34 of about 2 centimeters. However, this overall length and the number of windings of the coil can be varied as needed to provide the desired length of antenna coil 118.

In one embodiment of the present invention, flat wire 118 is made of a flat ribbon of copper or silver and can be plated with a highly conductive material. The ribbon can be 0.02 inches wide and 0.006 inches thick. Flat wire 118 has a physical length of 4.5 inches, which when coiled provides a total length for first coil wire section 140 and second coil wire section 142 of 2 centimeters.

The location along coil 118 of an electrical connection between first coil section 140 and capacitor 120 corresponds to a tap point used for impedance matching. Specifically, a tap point is selected along coil 118 so that an impedance presented between the tap point and annular collar 116 (corresponding to the point of electrical connection between coil 118 and inner conductor 100) matches the characteristic impedance of coaxial cable 41. As shown in FIG. 7, in this embodiment, the tap point is located at the end of first coil section 140 of coil 118. However, the tap point can be located nearer to annular collar 116 as necessary to obtain the required impedance match.

The impedance of either first coil section 140 or second coil section 142 also includes an inductive component which is eliminated by providing a series capacitance such as capacitor 120. Accordingly, tubular capacitor 120 serves to counteract a reactive component of antenna 34, thereby providing a fifty (50) Ohm resistive impedance match between coaxial cable 41, microwave generating source 40, and antenna 34.

Tubular capacitor 120 preferably has a value of about 2.7 pF and can be obtained from Coors Ceramics Co. of Golden, Colo. Capacitor 120 and preferably is sized to fit over an inner conductor 100 having an inner diameter of about 0.089 to 0.012 inches has a length of 0.125 inches, an outer diameter of about 0.045 inches, and an inner diameter of about 0.025 inches. Tubular capacitor 120 is substantially similar in design to a tubular capacitor described and shown in Rudie et al. U.S. Pat. No. 5,370,677, which is hereby incorporated by reference, and is mounted and connected to the inner conductor 100 and flat wire antenna coil 118 in a manner substantially similar to that described in Rudie et al. U.S. Pat. No. 5,370,677.

While the preferred dimensions for reduced diameter portion 110 have been identified above, the relatively smaller radial dimensions of reduced diameter portion 110 of inner insulator 102 could result in a characteristic impedance different than 50 Ohms. The characteristic impedance (Zo) can be calculated with the following equation:

$$Z_o = \frac{138}{\sqrt{\epsilon_r}} \log_{10}\left(\frac{D}{d}\right)$$

where Er is the relative dielectric constant of the inner insulator 102, D is the inner dimaeter of outer conductor 104, and d is the outer diameter of inner conductor 100. Accordingly, a characteristic impedance of 50 Ohms can be maintained with a reduced diameter portion 110 by adjusting the ratio of D/d (e.g., reducing d), by selecting an appropriate relative dielectric constant ($\epsilon_r$), or by adjusting both the ratio D/d and the relative dielectric constant ($\epsilon_r$). Alternatively, any resulting impedance mismatch resulting from the altered diameter of reduced diameter portion 110 of inner insulator 102 can be remedied by selecting an appropriate tap point location and a corresponding capacitor valve for capacitor 120.

Finally, antenna 34 can include platinum or gold bands located adjacent either or both ends of the flat wire antenna coil 118 to facilitate positioning of antenna 34 and catheter 28 within the cardiovascular system since the gold bands will substantially improve visualization of antenna 34 under fluoroscopy.

Antenna 34 generally has a helical dipole construction similar to the helical dipole construction of a microwave antenna described and shown in Rudie et al., U.S. Pat. Nos. 5,300,099 and 5,370,677, which are hereby incorporated by reference. Accordingly, the helical dipole construction of antenna 34 of the present invention has an effective electrical length generally equal to one-half of the wave length of the radiation emitted in the surrounding medium, e.g., the catheter shaft and surrounding tissue. Because of the helical dipole construction of antenna 34, in accordance with Rudie U.S. Pat. Nos. 5,300,099 and 5,370,677, antenna 34 can have different physical lengths yet have the same effective electrical length to produce a consistent and predictable pattern of radiation.

However, microwave antenna 34 of the present invention has its own unique advantages. Foremost, in order to minimize the profile of the cardiovascular catheter 28 and antenna 34 located therein, the antenna 34 and coaxial cable 41 are configured and arranged so that the antenna 34 has an outer diameter that is no greater than an outer diameter of the coaxial cable 41. This arrangement is achieved through a combination of features. First, inner insulator 102 is modified adjacent a distal end of coaxial cable 41 into a reduced diameter portion 110 along the length of the antenna 34, and outer insulator 106 of coaxial cable 41 is replaced with outer insulating tube sections 112 and 114. Second, flat wire coil 118 is located distally beyond the end of outer insulator 106 of coaxial cable 41 so that no portion of coil 118 extends about outer insulator 106 of coaxial cable 41.

However, with this arrangement, the point of electrical connection between inner conductor 104 and coil 118 can no longer be placed on the outer insulator 106 (as in the Rudie et al. patents) but instead needs to be located distally beyond a distal end of outer insulator 106. Accordingly, annular collar 116 is positioned to serve as the point of electrical connection between inner conductor 100 and coil 118 with outer insulator tube sections 112 and 114 being positioned on opposite sides of annular collar 116. This arrangement minimizes the length of the antenna portion of cardiovascular catheter 28 so that catheter 28 can be maneuvered more easily within the small confines of the cardiovascular system.

In combination, these modifications to the antenna disclosed in Rudie et al. U.S. Pat. Nos. 5,300,099 and 5,370,677 produce a microwave antenna 34 of the present invention that has substantially the same operating characteristics of the antenna disclosed in the Rudie et al. patents yet has an outer diameter no greater than an outer diameter of coaxial cable 41 to provide a low profile for cardiovascular and arterial applications. The antenna 34 also has a physical length which has been minimized to improve the maneuverability of the catheter 28.

Figure 8:
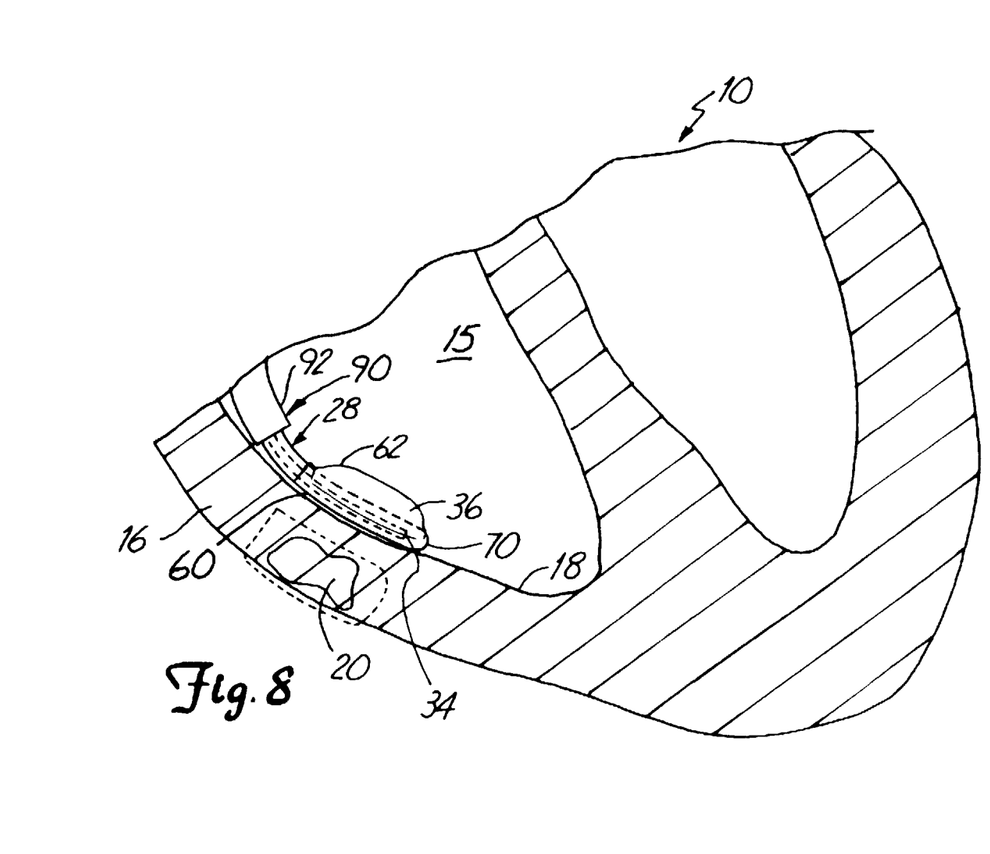
FIG. 8 is a partial sectional view of a catheter of the present invention as disposed within a ventricle of a heart for applying microwave thermal ablation therapy to the ventricle wall.
Figure 9:
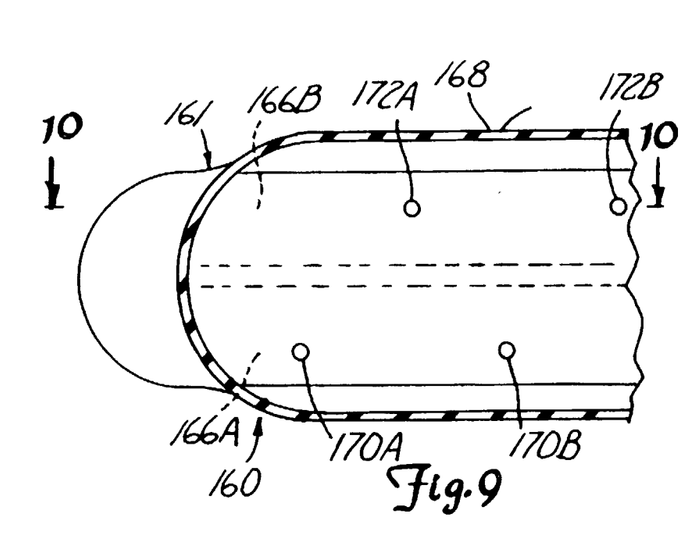
FIG. 9 is a plan view of an alternate embodiment of second side of the catheter shown in FIG. 6.

FIG. 8 shows an enlarged view of the ventricle 14 of FIG. 1 with catheter 28 properly positioned within ventricle 14. In use, catheter 28 is maneuvered into ventricle 14 through guide catheter 90. Guide catheter 90 has a design suitable for passage through a vascular system, so that a distal end 92 of guide catheter 90 can rest supportedly adjacent ventricle wall 16 to stably support catheter 28 adjacent wall 16.

Catheter 28 is inserted into guide catheter 90 from outside the body at a remote location (e.g., femoral artery) in a manner well known in the art. Catheter 28 is advanced through guide catheter 90 with cooling balloon 36 in its deflated state (shown in phantom in FIG. 2), which provides catheter 28 with a low profile to facilitate insertion and advancement of catheter 28 through guide catheter 90. Catheter shaft 28 is advanced through guide catheter 90 until distal end 54 is positioned within ventricle 14 as shown in FIG. 8. In this position, first side 60 of shaft 32 and cooling fluid intake lumens 76A, 76B are oriented toward ventricle wall 16 while second side 62 of shaft 32 with cooling fluid exhaust lumens 78A, 78B and cooling balloon 36 are oriented toward blood 15.

Next, cooling system 38 is operated to provide a continuous flow of cooling fluid through cooling fluid intake lumens 76A, 76B, cooling fluid exhaust lumens 78A, 78B, and cooling balloon 36. Cooling balloon 36 is inflated by the fluid through holes 80A and 82A from cooling exhaust lumens 78A and 78B.

At this point, microwave energy is selectively directed into target tissue 20 by energizing microwave antenna 34 with microwave generating source 40. Since cooling fluid exhaust lumens 78A, 78B and cooling balloon 36 absorb significant amounts of microwave energy while cooling fluid intake lumens 76A, 76B, absorb very little radiation, the radiation pattern applied to the surrounding tissues becomes asymmetrical with large amounts of microwave energy acting on target tissue 20 and almost no microwave energy acting on blood 15. As a result, a relatively large volume of tissue enveloping the damaged target tissue 20, adjacent catheter first side 60, is heated according to a time and temperature relationship that effectively necroses the damaged tissue 20 of ventricle wall 16 (which causes cardiac arrhythmias). In comparison, blood adjacent second side 62 remains below a necrosing time and temperature exposure, thereby eliminating the harmful effects of the heat (generated by microwave energy) to blood 15 and the remaining healthy structures of ventricle 14. For a complete discussion on the time and temperature relationship for causing necrosis of tissues, see Dickson et. al., Thermosensitivity of Neoplastic Tissues In Vivo, HYPERTHERMIA IN CANCER THERAPY, Chapter 5 (1983).

This preferential heating pattern created by catheter 28 allows microwave energy to be concentrated only at selective locations deep within the ventricle wall 16 (e.g., up to 2 cm) at damaged tissue 20 while protecting healthy tissues (e.g., blood 15) from necrosing temperatures (e.g., above 45° C.). After a desired amount of microwave energy has been applied to the damaged tissue 20 and the surrounding tissues have been allowed to return to normal body temperature, cooling system 38 can be turned off thereby permitting deflation of the cooling balloon 36. Once the cooling balloon 36 is deflated, the catheter 28 can be removed from ventricle 14 proximally through the guide catheter 90.

Intravascular catheter 28 of the present invention can be used as part of an intravascular microwave thermal therapy system substantially similar to the transurethral microwave thermal therapy system described and shown in Rudie et al. U.S. Pat. No. 5,413,588 and hereby incorporated by reference.

The catheter of the present invention permits the application of microwave energy in a cardiovascular environment to ablate tissue lesions located deep (e.g., 2 cm) below a surface of the tissue without causing necrosis of surrounding healthy tissues. This capability is achieved by a combination of features including, amongst others, an efficient dipole helical antenna design and a microwave energy absorbing system. The antenna of the present invention minimizes reflective losses, provides good current carrying capability, and has an effective electrical length that can remain consistent despite different physical lengths of the antenna. The microwave energy absorbing system includes a pair of cooling fluid intake lumens, a pair of exhaust lumens and a cooling balloon, which complements the cooling exhaust lumens.

Performing a thermal therapy treatment on a cardiac wall with catheter 28 of the present invention has considerable advantages. Cooling balloon 36 in combination with cooling exhaust lumens 78A, 78B enables cooling fluid within catheter 28 to cool blood immediately adjacent catheter second side 62 via thermal conduction. At the same time, the cooling fluid within cooling balloon 36 and within cooling exhaust lumens 78A, 78B, absorbs a substantial amount of microwave energy (when microwave antenna 34 within antenna lumen 58 is energized) so that the temperature of blood adjacent second side 62 of shaft 32 will remain below a necrosing temperature as desired (e.g., below 45° C). In combination, the relatively large radial dimensions of the cooling balloon 36, and its relative position adjacent a microwave antenna on second side 62 of catheter 28 provides a cooling chamber that protects blood when a microwave antenna within lumen 58 is energized. Conversely, high levels of microwave energy are directed beyond the ventricle wall surface 18 into the ventricle wall 16 as cooling intake lumens 76A, 76B protect wall surface 18 from thermal damage without substantially absorbing microwave radiation directed toward target tissues. This enables tissue in target region 20 (FIG. 8) deep below the ventricle wall surface to be adequately necrosed while at the same time preserving blood passing by a side of the catheter opposite the target location.

In addition, cooling balloon 36 accentuates thermal conduction between cooling fluid within cooling balloon 36 and blood flowing through the ventricle since cooling balloon 36 has a wall thickness less than the cooling exhaust lumens 78A, 78B. This feature places cooling fluid into closer contact with blood within the ventricle thereby improving heat transfer away from blood within the ventricle.

The presence of cooling balloon 36 also effectively makes antenna lumen 58 nearer to shaft first side 60 than shaft second side 62 (adjacent distal shaft end 54), so that antenna lumen 58 becomes eccentric to a longitudinal axis of catheter 28 adjacent distal shaft end 54. This orientation effectively moves antenna 34 further away from blood adjacent shaft second side 62 to further reduce unwanted heating of blood 15.

The cooling balloon is capable of being deflated as well as inflated. When deflated, the cooling balloon gives the catheter an overall low profile which facilitates insertion and advancement of the catheter through the cardiovascular system for deployment in distally remote locations, e.g., arteries and chambers of the heart. Moreover, cooling balloon 36 surrounds catheter shaft 32 with expandable portion 82 being the only portion of cooling balloon 36 spaced from catheter outer surface 53. This arrangement permits deflated cooling balloon 36 to have a low profile making cooling balloon 36 highly resistant to separation from the catheter shaft 32 and facilitating rotation of catheter 28 within urethra 10. This arrangement also simplifies the need for an elaborate system to wrap balloon 36 in deflated state. Finally, the cooling balloon conveniently slip fits over the distal tip of the catheter shaft thereby permitting easy manufacture of the catheter and ensuring that the balloon is properly sealed against the catheter shaft to allow proper inflation and deflation.

In an alternate embodiment, interior surface of cooling balloon 36 can include a coating capable of reflecting microwave energy from antenna 34, which these can further reduce the amount of microwave energy directed outwardly on the catheter second side 62. Such coating materials can also be incorporated into shaft 32 as necessary to further prevent the emission of microwave energy in undesired locations. For example, the coating material could be incorporated into the distal tip end of shaft 32 or along the shaft 32 proximal of antenna 34 to minimize unwanted emission of microwave energy in those areas.

Alternative embodiments of a catheter of the present invention are illustrated in FIGS. 9-14. Catheter 160 shown in FIG. 9 has all the attributes and features of catheter 28 shown in FIGS. 2-8 except that catheter 160 includes a modified structure for communication between cooling exhaust lumens and a cooling balloon. Specifically, instead of the structure shown in FIG. 6, catheter 160 shown in FIG. 9 includes catheter shaft 161 having cooling exhaust lumens 166A and 166B, cooling balloon 168, and a first pair of holes 170A, 170B and a second pair of holes 172A, 172B. An outer wall of cooling exhaust lumen 166A includes holes 170A and 170B, which permit communication between cooling exhaust lumen 166A and an interior of cooling balloon 168. An outer wall of cooling exhaust lumen 166B includes holes 172A and 172B which permit communication between an interior of cooling balloon 168 and cooling exhaust lumen 166B. Cooling fluid enters cooling balloon 168 through holes 170A, 172A and exits cooling balloon 168 through holes 170B, 172B.

Figure 10:
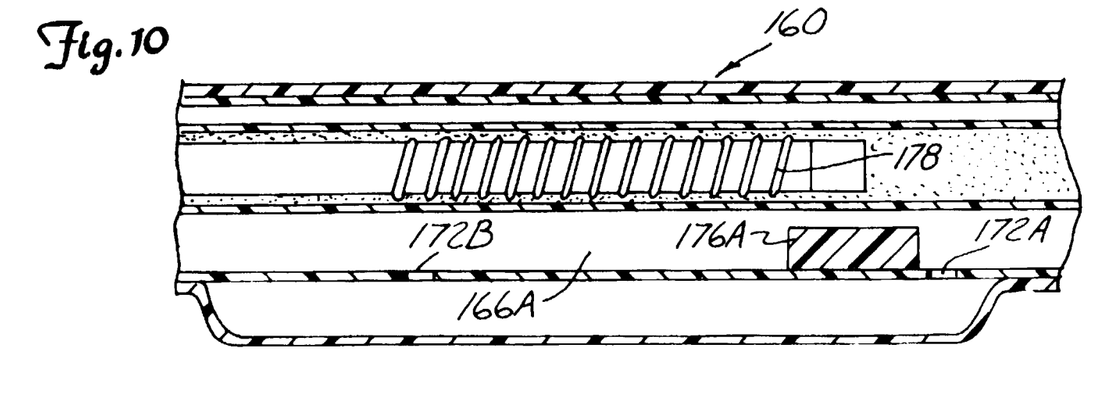
FIG. 10 is a sectional view of FIG. 9 as taken along lines 10—10.

Catheter 160 further includes restrictor 176A located between holes 170A and 170B and restrictor 176B between holes 172A and 172B, as shown in FIG. 10. For illustration purposes, only restrictor 176A located between holes 170A and 170B is shown. Restrictor 176A is positioned on an outer wall of cooling exhaust lumen 166A at a location selected to create a pressure differential between holes 170A, 170B thereby causing passive inflation and active circulation of fluid through cooling balloon 168. Restrictor 176A as shown in FIG. 10, is preferably located immediately adjacent hole 170A and proximal to antenna 178 so that the restrictor 176B does not affect a near field radiation emitted by the antenna 178. However, the restrictor 176A can be located at a more distal location adjacent the antenna 178 if desired. Restrictor 176A is formed and added to cooling exhaust lumen 166A by depositing adhesive on an inner surface of an outer wall of cooling exhaust lumen 166A at a desired location. Restrictor 176B is situated similar to restrictor 176A except being located between holes 172A and 172B in cooling exhaust lumen 166B.

In use, cooling fluid passing through cooling exhaust lumens 166A, 166B enters cooling balloon 168 through holes 170A and 172A thereby permitting passive inflation of cooling balloon 168. Restrictors 176A and 176B accentuate passive inflation of cooling balloon 168 and circulation of fluid therethrough by creating a pressure differential between holes 170A and 170B and between holes 172A and 172B. Holes 170B and 172B permit fluid to exit cooling balloon 168 into cooling exhaust lumens 166A and 166B for recirculation through a cooling system of catheter 160 (not shown).

Figure 11:
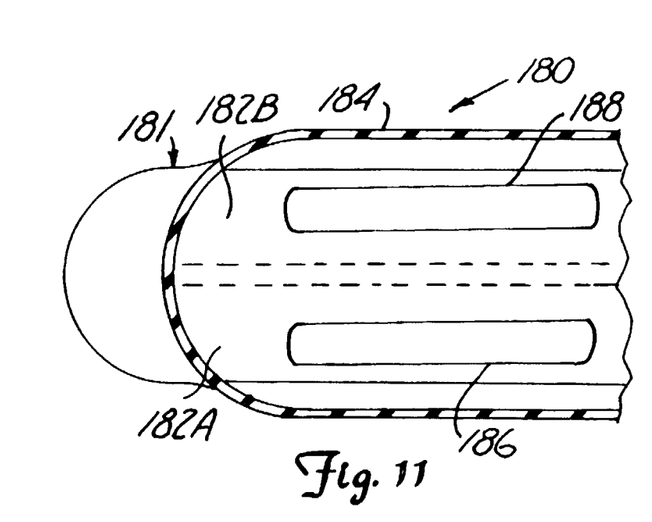
FIG. 11 is a plain view of an second alternate embodiment of second side of the catheter shown in FIG. 6.

FIG. 11 shows another modified catheter 180 of the present invention. Catheter 180 has all the attributes and features of catheter 28 shown in FIGS. 2-8 except that catheter 180 also includes a modified structure for communication between cooling exhaust lumens and cooling balloon 184. Specifically, instead of the structure shown in FIG. 6, catheter 180 includes catheter shaft 181 having cooling exhaust lumens 182A and 182B, cooling balloon 184, and a first slot 186 and a second slot 188. Slot 186 is an elongate hole formed in the side wall of catheter shaft defining exhaust lumen 182A while slot 186 is an elongate hole formed in the side wall of catheter shaft defining exhaust lumen 182B. Slot 186 permits unrestricted communication between cooling exhaust lumen 182A and an interior of cooling balloon 184 while slot 188 permits unrestricted communication between cooling exhaust lumen 182B and an interior of cooling balloon 184. This unrestricted communication facilitates relatively turbulent flow of cooling fluid within cooling balloon 184 thereby assuring active circulation of cooling fluid through the cooling balloon 184. Cooling balloon 184 is passively inflated and maintained in that state by controlling the rate of fluid flow into the cooling intake lumens (not shown) and the rate of fluid flow out of the cooling exhaust lumens 182A and 182B.

Figure 12:
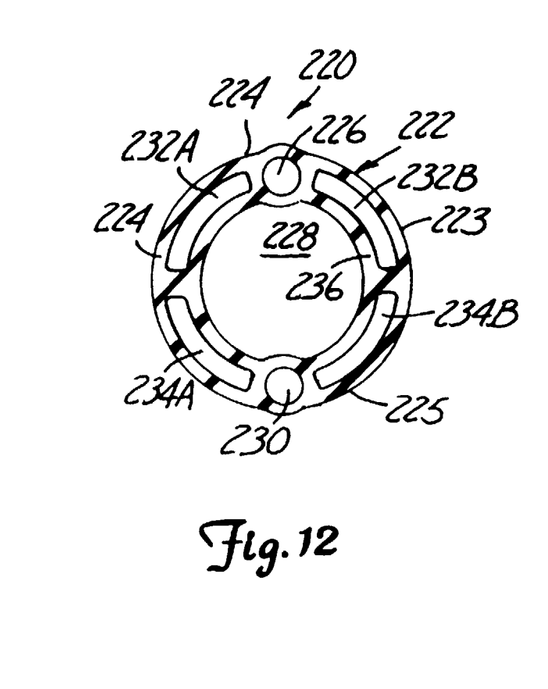
FIG. 12 is a sectional view of a shaft of an alternate embodiment of the catheter, similar to the view shown in FIG. 3.
Figure 13:
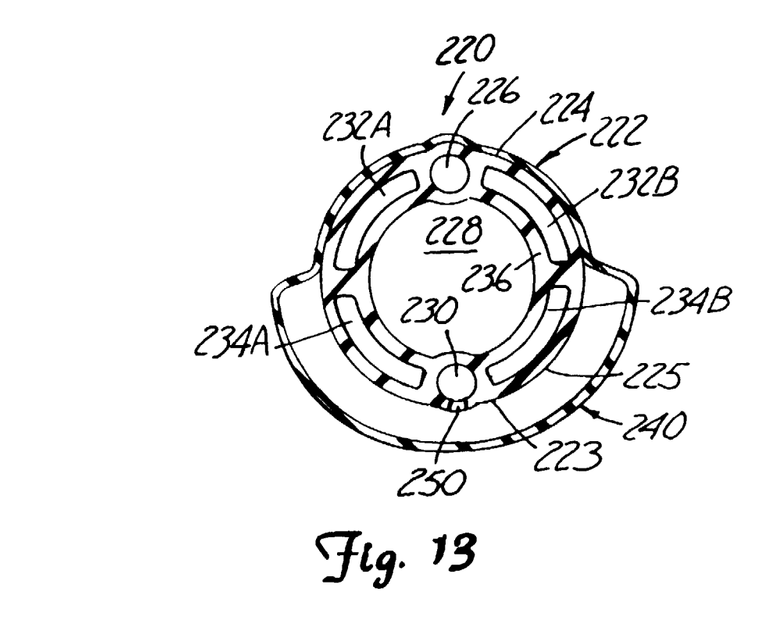
FIG. 13 is a sectional view of a shaft of an alternate embodiment of the catheter, similar to the view shown in FIG. 5A.

Another embodiment of the present invention is shown in FIGS. 12-13. Catheter 220 is similar to catheter 29 of the present invention (shown in FIGS. 2-8) and has all the attributes and features of catheter 28 except that catheter 220 includes a fluid lumen for inflating a cooling balloon that is independent of cooling exhaust lumens of the catheter. As shown in FIG. 12, catheter 220 generally includes multi-lumen shaft 222 having outer surface 223 with first side 224 and second side 225. Shaft 222 also has a distal end and a proximal end similar to those shown for catheter 28 in FIG. 2. Distal end of shaft 222 is connected to a manifold for communication and operation with a complete thermal therapy system as previously described for catheter 28.

As shown in FIG. 12, multi-lumen shaft 222 includes temperature sensing lumen 226, microwave antenna lumen 228, cooling balloon inflation lumen 230, cooling fluid intake lumens 232A and 232B, and cooling exhaust lumens 234A and 234B. Lumens 226–234B are similar to the corresponding temperature sensing lumen 56, microwave antenna 58, cooling lumens 64A, 64B previously described for catheter 28 in association with FIG. 3. However, unlike catheter 28, catheter 220 further includes a cooling balloon inflation lumen 230 and includes cooling exhaust lumens 234A, 234B which have slightly different dimensions than cooling exhaust lumens 78A, 78B of catheter 28 (FIG. 3).

Cooling balloon inflation lumen 230 is positioned between cooling exhaust lumens 234A and 234B adjacent second side 225 on an opposite side of antenna lumen 228 from temperature sensing lumen 226. Cooling balloon inflation lumen 230 preferably has a generally circular cross-sectional shape with a diameter of about 0.040 inches. Cooling balloon inflation lumen 230 communicates with an inflation port in a manifold to permit inflation and deflation of cooling balloon 250.

Cooling fluid intake lumens 232A, 232B are positioned adjacent shaft first side 224 and have all the attributes and features of cooling intake lumens 64A, 64B (FIG. 3). Cooling fluid exhaust lumens 234A, 234B are positioned adjacent shaft second side 225 and have all the attributes and features of cooling exhaust lumens 66A, 66B except having a smaller arc to accommodate cooling inflation lumens 230 positioned between lumens 234A and 234B. In addition, cooling exhaust lumens 234A, 234B lack holes in their outer walls similar to holes 80A and 80B in cooling lumens 66A, 66B. (FIG. 6).

Cooling fluid intake lumens 232A and 232B communicate with cooling exhaust lumens 234A and 234B, respectively near a proximal end of catheter shaft 232. Cooling intake lumens 232A and 232B and cooling exhaust lumens 234A and 234B cooperate with a cooling system via manifold to provide a selectively controlled flow of fluid from cooling intake lumens 232A, 232B into cooling exhaust lumens 234A, and 234B during a treatment session. Fluid contained within exhaust lumens 234A and 234B selectively absorbs a portion of microwave energy emitted by a microwave antenna within antenna lumen 228 and cools tissue surrounding shaft second side 225 to aid in controlling the temperature of tissue adjacent catheter shaft second side 225 below necrosing levels (e.g., below 45° C.).

As further shown in FIG. 13, cooling balloon 240 surrounds shaft outer surface 223 on shaft second side 225. Cooling balloon 240 has all the attributes and features of cooling balloon 36 of catheter 28 (as previously described in association with FIGS. 2-8). As shown in FIG. 13, an outer wall of cooling balloon inflation lumen 230 includes hole 250. Hole 250 permits communication between cooling balloon inflation lumen 230 and an interior of cooling balloon 240 (shown inflated in FIG. 13). Accordingly, cooling balloon 240 is filled and inflated by the introduction of cooling fluid from cooling balloon inflation lumen 230 through hole 250.

Cooling inflation lumen 230 is independent of cooling exhaust lumens 234A, 234B enabling cooling balloon 240 to be inflated and deflated independently of fluid flow within cooling exhaust lumens 234A, 234B. This relationship provides an additional means of cooling and microwave absorption while permitting independent control of cooling fluid within cooling lumens 232A, 232B, and 234A, 234B. However, since cooling balloon 240 and cooling inflation lumen 230 do not permit recirculation of fluid within cooling balloon 240 while inflated, fluid within cooling exhaust lumens 234A, 234B are relied upon to carry heat away from cooling fluid within cooling balloon 240 via thermal conduction.

Although the present invention has been described with reference to preferred embodiments, workers skilled in the art will recognize that changes may be made in form and detail without departing from the spirit and scope of the invention.

What is claimed is:

1. A device for cardiovascular microwave thermal therapy, the device comprising, a catheter;

a coaxial cable carried by the catheter, the coaxial cable having a proximal end, a distal end, an outer insulator, an outer conductor, an inner insulator and an inner conductor, the coaxial cable further having a transition portion between the distal and proximal ends adjacent the distal end of the cable wherein the inner insulator has a reduced diameter portion adjacent the distal end of the cable;

a supplemental outer insulator tube disposed about the reduced diameter portion of the inner insulator, and disposed adjacent an end of the outer insulator of the coaxial cable;

an antenna extending from the distal portion of the coaxial cable and having a first section, a second section of equal length to the first section and a point intermediate to the first and second sections, the intermediate point electrically connected to the outer conductor, the antenna being disposed about the reduced diameter portion of the inner insulator; and impedance matching means connected to the inner conductor and to the second section for matching impedances of the antenna and the coaxial cable.

2. A device for cardiovascular microwave thermal therapy, the device comprising:

a catheter;

a coaxial cable, carried by the catheter, having a first end, a second end, an outer insulator, an outer conductor, an inner insulator and an inner conductor, the inner insulator portion having a reduced diameter portion adjacent the second end of the cable;

a supplemental outer insulator tube disposed about the reduced diameter portion of the inner insulator, and disposed adjacent an end of the outer insulator of the coaxial cable;

an electrical element disposed about the supplemental outer insulator at the second end to form a dipole antenna having a first section, a second section and a point intermediate to the first and second sections, the intermediate point electrically connected to the outer conductor, the electrical element being disposed about the reduced diameter portion of the inner insulator; and impedance matching means connected between the inner conductor and a tap point on the second section for matching impedances of the antenna and the coaxial cable.

3. The device of claim 2 wherein the tap point is located at an end of the second section of the electrical element.

4. The device of claim 2 and further comprising:

an annular electrically conductive collar disposed about the outer conductor along the reduced diameter portion of the inner insulator, the collar being connected to the electrical element and the outer conductor.

5. The device of claim 4 wherein the supplemental outer insulator further comprises a first portion and a second portion, the first portion having a first end and a second end with the first end being positioned adjacent an end of the outer insulator of the coaxial cable and the second end abutting against the annular collar, and the second portion having a first end and a second end with the first end abutting against the annular collar on a side opposite the first portion and| |the second end extending beyond an end of the coaxial cable.

6. The device of claim 5 wherein the second portion of the supplemental outer insulator tube includes a hole to permit introduction of solder therethrough to connect the electrical element to the impedance matching means.

7. The device of claim 2 wherein the outer insulator terminates adjacent a proximal end of the reduced diameter portion of the inner insulator.

8. The device of claim 2 wherein an outer diameter of the electrical element is no greater than the outer diameter of the outer insulator of the coaxial cable.

9. A device for cardiovascular microwave thermal therapy, the device comprising:

a catheter;

a coaxial cable, carried by the catheter for delivering microwave energy, the coaxial cable having an outer insulator, an outer conductor, an inner insulator, and an inner conductor, the inner insulator having a reduced diameter portion with the outer insulator terminating adjacent the reduced diameter portion;

a supplemental outer insulator tube disposed about the reduced diameter portion of the inner insulator, and disposed adjacent an end of the outer insulator of the coaxial cable;

an antenna for emitting the microwave energy delivered by the coaxial cable, the antenna having a first antenna section and a second antenna section which are connected together at an intermediate point to the first and second antenna sections, the intermediate point being electrically connected to the outer conductor of the coaxial cable, the antenna being disposed about the reduced diameter portion of the inner insulator; and impedance matching means associated with the inner conductor of the coaxial cable and the second antenna section for matching impedances of the antenna and the coaxial cable.

10. A device for microwave thermal therapy, the device comprising:

a catheter;

a coaxial cable, carried by the catheter, having an outer insulator, an outer conductor, an inner insulator and an inner conductor, the inner insulator having a reduced diameter portion with the outer insulator terminating adjacent the reduced diameter portion;

a supplemental outer insulating tube disposed about the reduced diameter portion, being adjacent to an end of the outer insulator;

an electrical element disposed about the supplemental outer insulating tube circumjacent to the reduced diameter portion of the inner insulator to form a dipole antenna having first and second antenna sections of equal effective electrical length for receiving electromagnetic energy from the coaxial cable and emitting an electromagnetic radiation pattern, the outer conductor of the cable being connected to a center point at which the first and second antenna sections meet; and impedance matching means associated with the inner conductor and one of the first and second sections for matching an impedance of the electrical element to a characteristic impedance of the coaxial cable.

11. The device of claim 10 wherein an outer diameter of the electrical element is no greater than an outer diameter of the outer insulator of the coaxial cable.

12. A device for cardiovascular microwave thermal therapy, the device comprising:

a catheter;

a coaxial cable, carried by the catheter, having a first end, a second end, an outer insulator, an outer conductor, an inner insulator and an inner conductor, the inner insulator portion having a reduced diameter portion adjacent the second end of the cable;

a helical dipole antenna having a first section, a second section and a point intermediate to the first and second sections, the intermediate point electrically connected to the outer conductor, the helical dipole antenna being disposed about the reduced diameter portion of the inner insulator and having an outer diameter no greater than an outer diameter of the coaxial cable; and impedance matching means associated with the inner conductor of the coaxial cable and the second antenna section for matching impedances of the antenna and the coaxial cable.

13. The device of claim 12 and further comprising:

an annular electrically conductive collar disposed about the outer conductor along the reduced diameter portion of the inner insulator, the collar being connected to the helical dipole antenna and the outer conductor.

14. The device of claim 13 and further comprising:

a supplemental outer insulator tube disposed about the reduced diameter portion of the inner insulator, and disposed adjacent an end of the outer insulator of the coaxial cable.

15. The device of claim 14 wherein the supplemental outer insulator further comprises a first portion and a second portion, the first portion having a first end and a second end with the first end being positioned adjacent an end of the outer insulator of the coaxial cable and the second end abutting against the annular collar, and the second portion having a first end and a second end with the first end abutting against the annular collar on a side opposite the first portion and the second end extending beyond an end of the coaxial cable.

16. The device of claim 15 wherein the second portion of the supplemental outer insulator tube includes a hole to permit introduction of solder therethrough to connect the helical dipole antenna to the impedance matching means.

17. The device of claim 16 wherein the outer insulator terminates adjacent a proximal end of the reduced diameter portion of the inner insulator.

18. A device for cardiovascular microwave thermal therapy, the device comprising:

a catheter;

a coaxial cable, carried by the catheter, having a first end, a second end, an outer insulator, an outer conductor, an inner insulator and an inner conductor, the inner insulator portion having a reduced diameter portion adjacent the second end of the cable;

a supplemental outer insulator tube disposed about the reduced diameter portion of the inner insulator, and disposed adjacent an end of the outer insulator of the coaxial cable;

an electrical element disposed about the supplemental outer insulator at the second end to form a dipole antenna having a first section, a second section and a point intermediate to the first and second sections, the intermediate point electrically connected to the outer conductor, the electrical element being disposed about the reduced diameter portion of the inner insulator; and a tubular capacitor having an inner conductive layer, an outer conductive layer and a dielectric layer between the inner conductive layer and the outer conductive layer, the inner conductive layer being electrically connected to the inner conductor of the coaxial cable and the outer conductive layer being electrically connected to the second section of the antenna for matching impedances of the antenna and the coaxial cable.

19. The device of claim 18 and further comprising:

an annular electrically conductive collar disposed about the outer conductor along the reduced diameter portion of the inner insulator, the collar being connected to the electrical element and the outer conductor.

20. The device of claim 19 wherein the supplemental outer insulator further comprises a first portion and a second portion, the first portion having a first end and a second end with the first end being positioned adjacent an end of the outer insulator of the coaxial cable and the second end abutting against the annular collar, and the second portion having a first end and a second end with the first end abutting against the annular collar on a side opposite the first portion and the second end extending beyond an end of the coaxial cable.

21. The device of claim 18 wherein the outer insulator terminates adjacent a proximal end of the reduced diameter portion of the inner insulator.

22. The device of claim 18 wherein an outer diameter of the electrical element is no greater than the outer diameter of the outer insulator of the coaxial cable.

* * * * *

UNITED STATES PATENT AND TRADEMARK OFFICE
CERTIFICATE OF CORRECTION

PATENT NO. : 5,776,176
DATED : JULY 7, 1998
INVENTOR(S) : ERIC N. RUDIE

It is certified that error appears in the above-indentified patent and that said Letters Patent is hereby corrected as shown below:

Title page, item [54], and column 1, line 2,
in the title delete second occurrence of
"FOR ARTERIAL"

Col. 1, line 31, delete "arrhythmlas", insert --arrhythmias--

Col. 2, line 60, delete "miminiizes", insert --minimizes--

Col. 3, line 9, delete "9", insert --1--

Col. 3, line 22, delete "plain", insert --plan--

Col. 3, line 35, delete "plain", insert --plan--

Col. 4, line 45, delete "thermnometry", insert --thermometry--

Col. 6, line 57, delete "SB", insert --5B--

Col. 7, line 14, delete "SA", insert --5A--

UNITED STATES PATENT AND TRADEMARK OFFICE
CERTIFICATE OF CORRECTION

PATENT NO. : 5,776,176
DATED : July 7, 1998
INVENTOR(S) : Eric N. Rudie

It is certified that error appears in the above-indentified patent and that said Letters Patent is hereby corrected as shown below:

Col. 9, line 29, delete "dimaeter", insert --diameter--

Col. 16, Line 14, delete "[ ]" between "and" and "the"

Signed and Sealed this

Twenty-eighth Day of September, 1999

Attest:

Q. TODD DICKINSON

*Attesting Officer*    Acting Commissioner of Patents and Trademarks